(12) United States Patent
Neuser et al.

(10) Patent No.: US 6,929,805 B2
(45) Date of Patent: Aug. 16, 2005

(54) ANALGESIC COMBINATION

(75) Inventors: Dieter Neuser, Langenfeld (DE);
Monika Fierus, Leverkusen (DE);
Wolfgang Wiehl, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/402,737

(22) PCT Filed: Apr. 2, 1998

(86) PCT No.: PCT/EP99/01995

§ 371 (c)(1),
(2), (4) Date: Oct. 8, 1999

(87) PCT Pub. No.: WO98/46235

PCT Pub. Date: Oct. 22, 1998

(65) Prior Publication Data

US 2001/0002999 A1 Jun. 7, 2001

(30) Foreign Application Priority Data

Apr. 15, 1997 (DE) .......................... 197 15 594

(51) Int. Cl.⁷ ................................ A61K 9/14
(52) U.S. Cl. ...................... 424/489; 424/400
(58) Field of Search ................. 424/400, 489, 424/472

(56) References Cited

U.S. PATENT DOCUMENTS

| | | | |
|---|---|---|---|
| 4,446,140 A | * 5/1984 | Nelson | 424/260 |
| 4,593,044 A | 6/1986 | Metz | 514/557 |
| 4,851,233 A | 7/1989 | Khan et al. | 424/480 |
| 5,064,858 A | 11/1991 | Sapse | 514/536 |
| 5,096,926 A | 3/1992 | Fiorini et al. | 514/596 |
| 5,451,409 A | 9/1995 | Rencher | 424/468 |
| 5,609,884 A | * 3/1997 | Desai | 424/468 |
| 5,637,320 A | * 6/1997 | Bourke et al. | 424/489 |
| 5,702,723 A | * 12/1997 | Griffin | 424/463 |

FOREIGN PATENT DOCUMENTS

| | | | |
|---|---|---|---|
| EP | 0 418 565 A2 | 3/1991 | .......... A61K/31/65 |
| EP | 0 535 841 A1 | 4/1993 | .......... A61K/31/485 |
| EP | 0 722 720 A1 | 7/1996 | ............ A61K/9/20 |
| GB | 1 026 502 | 4/1966 | |
| WO | WO 94/03160 | 2/1994 | |
| WO | WO 96/07400 | 3/1996 | ............ A61K/9/22 |
| WO | WO 96/29986 | 10/1996 | |

OTHER PUBLICATIONS

Chemical Abstracts, vol. 102, No. 7, 1984; Columbus, Ohio, US; abstract No. 55856, Shibata et al: "Effects of Combinations on Some Anti–Inflammatory Drugs with Lidocaine HCI on Inflammatory Pain" XP002076707 see abstract & Shibata et al: Shika Kiso Igakkai Zasshi, vol. 26, No. 3, 1984, pp. 872–881.

Kagan, et al., J.Int.Med.Res., 1982, 10, 443: "Two Lozenges Containing Benzocaine Assessed in the Relief of Sore Throat".

Schachtel, et al., Arch.Intern.Med., 1991, 151, 733ff.: "Caffeine as an Analgesic Adjuvant".

Schachtel, et al., Clin.Pharmacol.Ther., 1988, 44, 704ff: "Sore throat pain in the evaluation of mild analgesics".

Schachtel, et al., Clin.Pharmacol.Ther., 1994, 55, 464ff.: "A placebo–controlled model to assay the onset of action of nonprescription–strength analgesic drugs".

* cited by examiner

*Primary Examiner*—Gary Kunz
*Assistant Examiner*—Konata M. George
(74) *Attorney, Agent, or Firm*—Norris McLaughlin & Marcus PA

(57) ABSTRACT

The present invention relates to medicinal preparations which can be administered orally and contain a fixed combination of at least one locally acting analgesic with a rapid onset of action and at least one systemically acting analgesic with a sustained action.

28 Claims, No Drawings

ANALGESIC COMBINATION

This application is a 371 of PCT/EP98/01926, which was filed on Apr. 2, 1998.

The present invention relates to medicinal preparations which can be administered orally and contain a fixed combination of at least one locally acting analgesic with a rapid onset of action and at least one systemically acting analgesic with a sustained action.

Locally acting analgesics with a rapid onset of action which can be used, for example, in the form of sprays or pastilles are already known. Local anaesthetics of this type display their action after less than one minute but have only a short duration of action so that frequent remedication is necessary, which adversely affects safety and patient compliance.

Examples of particularly interesting locally acting analgesics which may be mentioned are the benzocaines. They inhibit impulse formation and conduction in nerves by blocking the flow of sodium.

Systemically acting analgesics, such as, for example, NSAIDs, in particular acetylsalicylic acid (ASA), represent another useful possibility for alleviating pain. These analgesics reduce the sensitivity of the nociceptors, and the alleviation of pain can be explained by the inhibition of prostaglandin synthesis. With most of these systemically acting analgesics, the maximum activity is not reached until after about 1–2 hours.

An object of the present invention is to satisfy the need, which has existed for a long time, to provide a preparation which can be administered orally and which combines, in a simple and reliable manner, an immediate analgesic action with a sustained action.

The active substances which can be used as locally acting analgesics (element A) are those which show a significant onset of action within a period of up to 10 minutes, preferably of 4 minutes, in particular of 1 minute and very particularly of 30 seconds.

The locally acting analgesics (combination element A) are expediently employed in amounts of from 0.5 to 100 mg, preferably 1 to 60 mg and, in particular, 2 to 30 mg, per individual administration form.

The combination according to the invention may contain one or more local anaesthetics as element A, for example 1, 2 or 3. Combinations with only one compound of element A are of particular interest.

The active substances of element A are substantially known. Particularly suitable examples which may be mentioned are ester-type local anaesthetics such as benzocaine, amethocaine, amylocaine, butacaine, butoxycaine, butyl aminobenzoate, chloroprocaine, chlormecaine, cyclomethycaine, isobutamben, meprylcaine, oxybuprocaine, procaine, propipocaine, proxymetacaine, tricaine etc. Mention may likewise be made of anilide-type local anaesthetics such as lidocaine, bupivacaine, butanilicaine, carticaine, cinchocaine, clibucaine, etidocaine, mepivacaine, oxethazaine, prilocaine, ropivacaine, ethyl p-piperidinoacetyl-aminobenzoate, tolycaine, trimecaine, vadocaine, etc.

It is also possible to employ other local anaesthetics such as, for example, pramoxine or essential oils such as menthol or eucalyptus oil.

The systemically acting analgesics which can be employed as element B are likewise substantially known. Mention may preferably be made of non-steroidal antiinflammatory drugs (NSAIDs) such as, for example, phenylacetic acid derivatives such as aceclofenac, alclofenac, bromofenac, diclofenac, fenclofenac etc., arylacetic acid derivatives such as acemetacin, amfenac sodium, bendazac, glucametacin, oxametacin, etc., para-aminophenol derivatives such as acetanilide, etc., propionic acid derivatives such as alminoprofen, ibuprofen, ketoprofen, flurbiprofen, naproxen, oxaprozin, salicylic acid derivatives such as acetylsalicylic acid (ASA), aluminium ASA and other salts, diflunisal, etersalate, fosfosal, salol, salsalate, salacetamide, etc., pyrazolone derivatives such as amidopyrine, dipyrone etc., oxycam derivatives such as droxicam, isoxicam, piroxicam etc., phenylbutazone derivatives such as azapropazone, bumadizone calcium, oxyphenbutazone etc., pyranoindoleacetic acid derivatives such as etodolac etc., anthranilic acid derivatives such as glafenine, Na meclofenamate, mefenamic acid, morniflumate etc., indole derivatives such as indomethacin etc., paracetarnol and paracetamol derivatives and other NSAIDs such as anirolac, benzpiperylone, benzydamine hydrochloride, Na butibufen, chlorthenoxazine, cinmetacin, clonixin, cloracetadol, difenpiramide, diproqualone, etenzamide, famprofazone, flupirtine maleate, ibuproxam, indoprofen, isamfazone, meloxicam, metiazinic acid, metifenazone, nifenazone, niflumic acid, mimesulide, pirazolac, pranoprofen, proquazone, protizinic acid, ramifenazone etc.

The systemically acting analgesics of element B are employed according to the invention in amounts of from 5 to 1500 mg, preferably 8 to 1000 mg, in particular 10 to 800 mg, per dosage form.

The local analgesics preferably employed as element A are rapidly acting and have an optimal duration of action lasting 0.5 to 120 minutes, preferably 2 to 60 minutes, in particular 5 to 30 minutes. The systemic analgesics preferably used as element B are those where a significant action has its onset after 15 minutes and lasts for up to 24 hours, preferably those whose action has its onset after 20 minutes and lasts for up to 12 hours, in particular up to 8 hours.

Particularly interesting combinations according to the invention are those which contain as element A an ester-type local anaesthetic, in particular benzocaine, and contain as element B propionic acid derivatives or salicylic acid derivatives, in particular ASA.

Preferred systemic analgesics are those which have a duration of action of at least 3 hours.

The combination according to the invention is particularly suitable for treating inflammatory and/or painful disorders of the oropharynx, in particular for treating pharyngitis, laryngitis, tonsillitis, stomatitis, gingivitis of a variety of aetiologies. The combination product according to the invention is expediently administered orally.

The combination can be employed in conventional formulations, the intention being that the local anaesthetic is released first, and it being possible for the systemically acting analgesic where appropriate also to be present in depot form. The following may be mentioned as examples of such preparations: press-coated tablets, coated pastilles, chewing gum, hard caramel with liquid, semisolid or solid core. They are produced by conventional methods using customary ancillary substances.

EXAMPLES

Example 1

A tablet of the following composition may be mentioned by way of example:

ASA core tablet:

500 mg of ASA are compressed with 30 mg of ascorbic acid, 75 mg of sucrose, 47 mg of microcrystalline cellulose, 2 mg of saccharin (550×) and 6 ml of orange juice flavouring to give a tablet with a total weight of 660 mg. These core tablets are coated uniformly with a benzocaine-containing coating syrup, applying a total of about 5 mg of benzocaine and 602 mg of coating syrup. The aforementioned tablet shows a marked analgesic action only two minutes after intake, and this is sustained for a period of more than 3 hours.

Example 2

A core tablet containing 300 mg of naproxen is coated with a coating syrup which contains 500 mg of lidocaine in analogy to Example 1. This combination preparation shows an onset of action after 2 minutes and a duration of action of more than 6 hours.

What is claimed is:

1. A preparation which can be administered orally and contains a fixed combination of at least one locally acting analgesic with a rapid onset of action (element A) with at least one systemically acting analgesic with a sustained action (element B), wherein element A and element B provide distinct active analgesic compounds.

2. A preparation according to claim 1, characterized in that the active substance employed as element A shows an optimal duration of action of from 0.5 to 120 minutes, and the active substance employed as element B has an action of from 15 minutes up to 24 hours.

3. A preparation according to claim 1, characterized in that elements A and B are selected so that the fixed combination has a duration of action of from 2 minutes up to 12 hours.

4. Process for producing a preparation according to claim 1, characterized in that the fixed combination of an active substance of element A and an active substance of element B are converted together with conventional ancillary substances and carrier into a suitable administration form.

5. The preparation according to claim 1, which is in the form of a press-coated tablet.

6. The preparation according to claim 1, which is in the form of coated pastille.

7. The preparation according to claim 1, which is in the form of a chewing gum.

8. The preparation according to claim 1, which is in the form of a hard caramel with a liquid, semisolid or solid core.

9. The preparation according to claim 1, which is in the form of a inner core tablet coated with an outer coating, wherein the outer coating comprises the at least one locally acting analgesic with a rapid onset of action (element A), the inner core tablet comprises the at least one systemically acting analgesic with a sustained action (element B), and wherein elements A and B are provide distinct active analgesic compounds.

10. A preparation which can be administered orally and is in the form of a inner core tablet coated with an outer coating, wherein the outer coating comprises at least one locally acting analgesic with a rapid onset of action (element A) selected from the group consisting of benzocaine, amethocaine, amylocaine, butacaine, butoxycaine, butyl aminobenzoate, chloroprocaine, chlormecaine, cyclomethycaine, isobutamben, meprylcaine, oxybuprocaine, procaine, propipocaine, proxymetacine, tricaine, lidocaine, bupivacaine, butanilicaine, carticaine, cinchocaine, clibucaine, etidocaine, mepivacaine, oxethazaine, prilocaine, ropivacaine, ethyl p-piperidinoacetyl-aminobenzoate, tolycaine, trimecaine and vadocaine, and the inner core tablet comprises at least one systemically acting analgesic with a sustained action (element B) selected from the group consisting of aceclofenac, alclofenac, bromofenac, diclofenac, fenclofenac, acemetacin, amfenac sodium, bendazac, glucametacin, oxametacin, acetanilide, alminoprofen, ibuprofen, ketoprofen, flurbiprofen, naproxen, oxaprozin, acetyl salicylic acid, salts of acetylsalicylic acid, diflunisal, etersalate, fosfosal, salol, salsalate, salacetamide, amidopyrine, dipyrone, droxicam, isoxicam, piroxicam, azapropazone, bumadizone calcium, oxyphenbutazone, etodolac, galfenine, sodium meclofenamate, mefenamic acid, momiflumate, idomethacin, paracetamol, paracetamol derivatives, anirolac, benzpiperylone, benzydamine hydrochloride, sodium butibufen, chlorthenoxazine, cinmetacin, clonixin, cloracetadol, difenpiramide, diproqualone, etenzamide, famprofazone, flupirtine maleate, ibuproxam, indoprofen, isamfazone, meloxicam, metiazinic acid, metifenazone, nifenazone, niflumic, mimesulide, pirazolac, pranoprofen, proquazone, protizinic acid and ramifenazone.

11. The preparation according to claim 10, which is in the form of an inner core tablet coated with an outer coating, wherein the outer coating comprises benzocaine as the at least one locally acting analgesic with a rapid onset of action (element A), and the inner core tablet comprises acetylsalicylic acid or salt thereof as the at least one systemically acting analgesic with a sustained action (element B).

12. A method of alleviating pain in a patient in need thereof comprising administering to said patient a preparation according to claim 1.

13. A preparation which can be administered orally and contains a fixed combination of at least one locally acting analgesic with a rapid onset of action (element A) with at least one systemically acting analgesic with a sustained action (element B), wherein element A and element B provide distinct active analgesic compounds, and the preparation is formulated such that element A is released from the preparation before element B upon oral administration.

14. A method of alleviating pain in a patient in need thereof comprising administering to said patient a preparation according to claim 10.

15. A method of alleviating pain in a patient in need thereof comprising administering to said patient a preparation according to claim 13.

16. An analgesic preparation comprising,
   a) element A, which comprises at least one locally acting analgesic having a rapid onset of action,
   b) element B, which comprises a core tablet having at least one systemically acting analgesic having sustained action, and wherein element A is a coating that encloses at least a portion of said core tablet's surface area and wherein element A and element B provide distinct active analgesic compounds.

17. The analgesic preparation of claim 16, wherein element A entirely encloses element B.

18. The analgesic preparation of claim 16, wherein element A encloses less than 100% of element B's surface area.

19. The analgesic preparation of claim 16, wherein the at least one locally acting analgesic is selected from the group consisting of benzocaine, amethocaine, amylocaine, butacaine, butoxycaine, butyl aminobenzoate, chloroprocaine, chlormecaine, cyclomethycaine, isobutamben, meprylcaine, oxybuprocaine, procaine, propipocaine, proxymetacine, tricaine, lidocaine, bupivacaine, butanilicaine, carticaine, cinchocaine, clibucaine, etidocaine, mepivacaine, oxethazaine, prilocaine, ropivacaine, ethyl p-piperidinoacetyl-aminobenzoate, tolycaine, trimecaine and vadocaine.

20. The analgesic preparation of claim 16, wherein the at least one systemically acting analgesic having sustained action, is selected from the group consisting of aceclofenac, alclofenac, bromofenac, diclofenac, fenclofenac, acemetacin, amfenac sodium, bendazac, glucametacin, oxametacin, acetanilide, alminoprofen, ibuprofen, ketoprofen, flurbiprofen, naproxen, oxaprozin, acetyl salicylic acid, salts of acetylsalicylic acid, diflunisal, etersalate, fosfosal, salol, salsalate, salacetamide, amidopyrine, dipyrone, droxicam, isoxicam, piroxicam, azapropazone, bumadizone calcium, oxyphenbutazone, etodolac, galfenine, sodium meclofenamate, mefenamic acid, morniflumate, idomethacin, paracetamol, paracetamol derivatives, anirolac, benzpiperylone, benzydamine hydrochloride, sodium butibufen, chlorthenoxazine, cinmetacin, clonixin, cloracetadol, difenpiramide, diproqualone, etenzamide, famprofazone, flupirtine maleate, ibuproxam, indoprofen, isamfazone, meloxicam metiazinic acid, metifenazone, nifenazone, niflumic acid, mimesulide, pirazolac, pranoprofen, proquazone, protizinic acid and ramifenazone.

21. An analgesic preparation comprising an element A and an element B, wherein,
a) element A comprises at least one locally acting analgesic having a rapid onset of action, said at least one locally acting analgesic being selected from the group consisting of benzocaine, amethocaine, amylocaine, butacaine, butoxycaine, butyl aminobenzoate, chloroprocaine, chlormecaine, cyclomethycaine, isobutamben, meprylcaine, oxybuprocaine, procaine, propipocaine, proxymetacine, tricaine, lidocaine, bupivacaine, butanilicaine, carticaine, cinchocaine, clibucaine, etidocaine, mepivacaine, oxethazaine, prilocaine, ropivacaine, ethyl p-piperidinoacetylaminobenzoate, tolycaine, trimecaine and vadocaine; and
b) element B comprises at least one systemically acting analgesic having sustained action, and wherein the locally acting analgesic having a rapid onset of action that comprises element A is an analgesic different from the analgesic in element B.

22. An analgesic preparation comprising an element A and an element B, wherein,
a) element A comprises at least one locally acting analgesic having a rapid onset of action; and
b) element B comprises at least one systemically acting analgesic having sustained action, wherein said at least one systemically acting analgesic is selected from the group consisting of aceclofenac, alclofenac, bromofenac, diclofenac, fenclofenac, acemetacin, amfenac sodium, bendazac, glucametacin, oxametacin, acetanilide, alminoprofen, ibuprofen, ketoprofen, flurbiprofen, naproxen, oxaprozin, acetyl salicylic acid, salts of acetylsalicylic acid, diflunisal, etersalate, fosfosal, salol, salsalate, salacetamide, amidopyrine, dipyrone, droxicam, isoxicam, piroxicam, azapropazone, bumadizone calcium, oxyphenbutazone, etodolac, galfenine, sodium meclofenamate, mefenamic acid, morniflumate, idomethacin, paracetamol, paracetamol derivatives, anirolac, benzpiperylone, benzydamine hydrochloride, sodium butibufen, chlorthenoxazine, cinmetacin, clonixin, cloracetadol, difenpiramide, diproqualone, etenzamide, famprofazone, flupirtine maleate, ibuproxam, indoprofen, isamfazone, meloxicam, metiazinic acid, metifenazone, nifenazone, niflumic acid, mimesulide, pirazolac, pranoprofen, proquazone, protizinic acid and ramifenazone, and wherein element A and element B provide distinct active analgesic compounds.

23. An analgesic preparation comprising,
a) element A, which further comprises at least one locally acting analgesic having a rapid onset of action,
b) element B, which further comprises at least one systemically acting analgesic having sustained action,
and wherein element A and element B provide distinct active analgesic compounds, and are each independently provided in said preparation in a manner that resist commingling of said element A and element B until administration of said preparation to a subject.

24. The analgesic preparation of claim 23, wherein the preparation is a chewable gum or chewable candy that further comprises at least one distinct region having element A, and at least one distinct region having element B, and wherein said regions do not commingle prior to administering said preparation to a subject.

25. The analgesic preparation according to claim 23, wherein the preparation is a solid form of candy, having a liquid center.

26. The analgesic preparation of claim 24, wherein the regions are juxtaposed in a pattern of bar-shaped stripes.

27. The analgesic preparation of claim 24, wherein the regions comprising each of said element A or B, further comprise layers, stacked one on top of the other.

28. A preparation that can be administered orally and comprises a fixed combination of at least one locally acting ester-type anesthetic having a rapid onset of action (element A), and further comprising at least one systemically acting analgesic with a sustained action (element B), wherein,
(i) element A and element B provide distinct active analgesic compounds, and
(ii) element A comprises an outer coating that envelopes a core tablet comprising element B.

* * * * *

UNITED STATES PATENT AND TRADEMARK OFFICE
CERTIFICATE OF CORRECTION

PATENT NO. : 6,929,805 B2 Page 1 of 1
APPLICATION NO. : 09/402737
DATED : August 16, 2005
INVENTOR(S) : Neuser et al.

It is certified that error appears in the above-identified patent and that said Letters Patent is hereby corrected as shown below:

Column 3, Line 51, "are provide" should read -- are provided --

Column 4, Line 11, "momiflumate" should read -- morniflumate --

Column 4, Line 16, "niflumic," should read -- niflumic acid --

Column 5, Line 18, "meloxicam metiazinic" should read -- meloxicam, metiazinic --

Signed and Sealed this

Twenty-ninth Day of May, 2007

JON W. DUDAS
*Director of the United States Patent and Trademark Office*